United States Patent [19]

Bernardi et al.

[11] 4,089,862
[45] May 16, 1978

[54] PYRIDYL SUBSTITUTED ERGOLINE DERIVATIVES

[75] Inventors: Luigi Bernardi; Carlo Elli; Giovanni Falconi; Rosella Ferrari, all of Milan, Italy

[73] Assignee: Societa' Farmaceutici Italia S.p.A., Milan, Italy

[21] Appl. No.: 756,725

[22] Filed: Jan. 4, 1977

[30] Foreign Application Priority Data

Jan. 9, 1976 United Kingdom ............... 00738/76

[51] Int. Cl.$^2$ .......................................... C07D 457/02
[52] U.S. Cl. .................................. 260/285.5; 424/261
[58] Field of Search ...................................... 260/285.5

[56] References Cited

U.S. PATENT DOCUMENTS

| | | | |
|---|---|---|---|
| 3,014,909 | 12/1961 | Rutschmann et al. | 260/285.5 |
| 3,833,585 | 9/1974 | Stadler et al. | 260/285.5 |
| 3,901,891 | 8/1975 | Kornfeld et al. | 260/285.5 |
| 3,996,228 | 12/1976 | Arcari et al. | 260/285.5 |
| 4,004,011 | 1/1977 | Hauth et al. | 260/285.5 |

FOREIGN PATENT DOCUMENTS

| | | | |
|---|---|---|---|
| 1,470,217 | 12/1969 | Germany | 260/285.5 |
| 463,524 | 11/1968 | Switzerland | 260/285.5 |

*Primary Examiner*—Donald G. Daus
*Assistant Examiner*—Mary Vaughn
*Attorney, Agent, or Firm*—Stevens, Davis, Miller & Mosher

[57] ABSTRACT

A process is disclosed for the preparation of a compound of the formula I

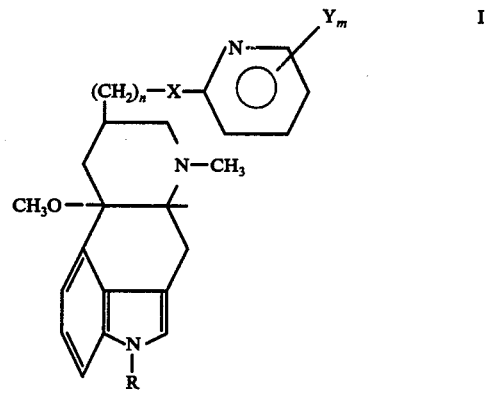

where R is hydrogen or methyl, X is sulphur or the NH group, Y is selected from the class consisting of methyl, methoxy, chlorine, bromine, iodine, nitro or cyano, $m$ is 0, 1 or 2, and $n$ is 1 or 2, characterized in that a compound of the formula II:

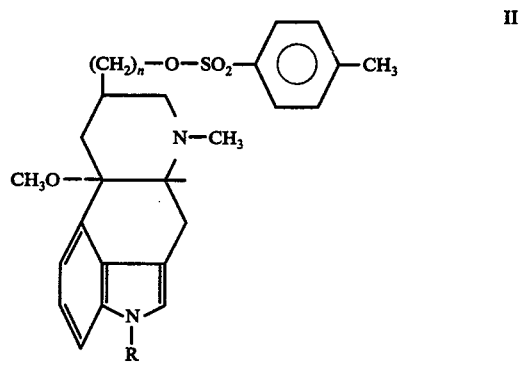

where R and $n$ have the above-mentioned meanings, is reacted in a suitable polar aprotic solvent, such as dimethylforamide or dimethylsulphoxide, under a nitrogen atmosphere and at a temperature between 50° and 100° C, with the sodium salt of an appropriate 2-aminopyridine or 2-mercaptopyridine to give, after evaporation of the solvent in vacuo, the desired compound of formula I which is then purified by methods known "per se".

The invention also includes the compounds of general formula I, where R, X, Y, $m$ and $n$ have the same meanings, and their pharmaceutically acceptable salts. These compounds have good alpha-adrenoyltic activity, and especially a very high and unexpected platelets aggregating inhibiting activity compared to e.g. nicergoline.

10 Claims, No Drawings

PYRIDYL SUBSTITUTED ERGOLINE DERIVATIVES

The present invention relates to new ergoline derivatives and to a new process for their preparation.

More particularly, the present invention relates to the preparation of ergoline derivatives of the general formula I:

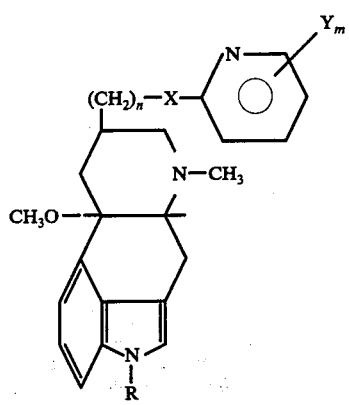

wherein R is hydrogen or methyl, X is sulphur or the NH group, Y is selected from the class consisting of methyl, methoxy, chlorine, bromine, iodine, nitro, cyano, m is 0, 1 or 2, and n is 1 or 2.

These compounds are prepared by reacting a tosylate of the general formula II:

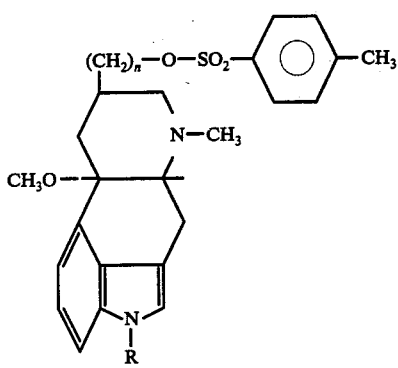

where R and n have the above-mentioned meanings, with the sodium salt of an appropriate 2-mercaptopyridine or an appropriate 2-aminopyridine, i.e., a 2-mercaptopyridine or a 2-aminopyridine having at most two pyridyl ring substituents corresponding to that desired in the final compound as shown by formula I.

The reaction is carried out in a suitable polar aprotic solvent, such as dimethylformamide or dimethylsulfoxide, under a nitrogen atmosphere and at a temperature between 50° and 100° C.

The compounds according to the present invention have good alpha-adrenolytic activity, but their importance is due to a very high and unexpected platelets aggregating inhibiting activity, as indicated in the table below where the inhibiting activity of said compounds is reported in comparison with the activity of a commercial alpha-adrenolytic ergoline derivative marketed by applicants' assignee, namely nicergoline (10-methoxy-1,6-dimethyl-8β-methanol-5-bromonicotinate; 355/347).

For the relevant study on the platelet aggregation "in vitro" herein, the turbidimetric method initially described by Born and Cross (J. Physiol. 168, 178, 1963) has been followed with some changes, principally due to the use of rabbit platelets, rather than human or pig platelets, as reported in their original work:

(1) Preparation of platelet-rich plasma (PRP) and platelet-poor plasma (PPP)

Male rabbits weighing 2.5–3.5 kg were used. Fifty four ml of blood were withdrawn from the carotid artery of rabbits anaesthetized with ether. The blood was gently mixed with six ml of 3.8% trisodium citrate as anticoagulant.

The PRP was obtained by centrifugation at 400 g for 10 minutes. The concentration of the platelets was adjusted to 250,000/mm$^3$ by diluting the PRP with PPP prepared by a second centrifugation of the blood samples for about 10 minutes at 2000 g.

The aggregation experiments were in general performed within 1–2 hr. from the time of blood collection.

(2) ADP induced platelet aggregation

In the cuvette of the aggregometer, reagents were added as follows:

0.8 ml PRP, 0.2 ml drug solution or saline, and 0.2 ml ADP (adenosine diphosphate) at the molar concentration of $2.2 \times 10^{-4}$.

The turbidimetry was checked after 1½, 3 and 6 minutes.

The inhibition of the aggregation is given in the table as percent of ADP controls at these three times. These data show that the new derivatives of the present invention are significantly more active than the reference standard, nicergoline (355/347), at all dose times.

TABLE

PERCENT INHIBITION OF PLATELET AGGREGATION AT VARIOUS TIMES (1'30" – 3' – 6') AFTER ADP

| 1 minute and 30 seconds | | | | | | |
|---|---|---|---|---|---|---|
| 355 γ | 347 | 893 | 894 | 897 | 925 | 926 |
| 200 | 40 | 63 | 100 | 89 | 100 | 100 |
| 100 | 24 | 58 | 61 | 62 | 50 | 61 |
| 50 | 11 | 31 | 22 | 31 | 16 | 25 |

| 3 minutes | | | | | | |
|---|---|---|---|---|---|---|
| 355 γ | 347 | 893 | 894 | 897 | 925 | 926 |
| 200 | 50 | 69 | 100 | 91 | 100 | 100 |
| 100 | 21 | 46 | 61 | 51 | 56 | 55 |
| 50 | 12 | 14 | 22 | 22 | 21 | 13 |

| 6 minutes | | | | | | |
|---|---|---|---|---|---|---|
| 355 γ | 347 | 893 | 894 | 897 | 925 | 926 |
| 200 | 60 | 71 | 100 | 92 | 100 | 100 |
| 100 | 33 | 52 | 71 | 56 | 65 | 65 |
| 50 | 22 | 7 | 29 | 25 | 30 | 17 |

Due to their anti-aggregating activity, the compounds of the present invention should prove useful in the treatment of many central and peripheral vascular diseases (e.g. cerebral and myocardial ischemias of thrombotic origin).

A number of examples showing in detail how the new compounds may be obtained are as follows:

EXAMPLE 1

N-(2'-pyridyl)-10α-methoxy-1,6-dimethylergoline-8β-methanamine (I, R=CH₃; n=1; X=NH; m=0 — (355/925)

To 7.5 mmol of 2-aminopyridine in 30 ml of anhydrous dimethylformamide, an equivalent of sodium hydride dispersion in mineral oil is added under nitrogen at 50° C.

After 2 hours, 3.75 mmol of 10α-methoxy-1,6-dimethylergoline-8β-methanol tosylate (II; R=CH₃; n=1) are added and the solution is kept at 60° C for 3 hours.

After evaporation of the solvent in vacuo, the residue is washed with pentane and chromatographed on alumina to give N-(2'-pyridyl)-10α-methoxy-1,6-dimethyl-8β-methanamine (55% yield), m.p. 209°–211° C.

EXAMPLE 2

N-(5'-nitro-2'-pyridyl)-10α-methoxy-1,6-dimethylergoline-8β-methanamine (I: R = CH₃; n = 1; X = NH; Y = 5-NO₂) - (355/892)

Operating as in Example 1, but employing 2-amino-5-nitropyridine, N-(5'-nitro-2'-pyridyl)-10α-methoxy-1,6-dimethylergoline-8β-methanamine (57% yield), m.p. 160°–163° C, is obtained.

EXAMPLE 3

N-(3'-nitro-2'-pyridyl)-10α-methoxy-1,6-dimethylergoline-8β-methanamine (I; R = CH₃; n = 1; X = NH; Y = 5-NO₂) - (355/901)

Operating as in Example 1, but employing 2-amino-3-nitropyridine, N-(3'-nitro-2'-pyridyl)-10α-methoxy-1,6-dimethylergoline-8β-methanamine (60% yield), m.p. 150°–152° C, is obtained.

EXAMPLE 4

N-(5'-bromo-2'-pyridyl)-10α-methoxy-1,6-dimethylergoline-8β-methanamine (I; R = CH₃; n = 1; X = NH; Y = 5-Br) - (355/893)

Operating as in Example 1, but employing 2-amino-5-bromopyridine, N-(5'-bromo-2'-pyridyl)-10α-methoxy-1,6-dimethylergoline-8β-methanamine (45% yield), m.p. 163°–165° C, is obtained.

EXAMPLE 5

N-(4'-methyl-2'-pyridyl)-10α-methoxy-1,6-dimethylergoline-8β-methanamine (I; R = CH₃; n = 1; X = NH; Y = 4-CH₃) - (355/894)

Operating as in Example 1, but employing 2-amino-4-methylpyridine, N-(4'-methyl-2'-pyridyl)-10α-methoxy-1,6-dimethylergoline-8β-methanamine (48% yield), m.p. 201°–203° C, is obtained.

EXAMPLE 6

N-(5'-methyl-2'-pyridyl)-10α-methoxy-1,6-dimethylergoline-8β-methanamine (I; R = CH₃; n = 1; X = NH; Y = 5-CH₃) - (355/896)

Operating as in Example 1, but employing 2-amino-5-methylpyridine, N-(5'-methyl-2'-pyridyl)-10α-methoxy-1,6-dimethylergoline-8β-methanamine (49% yield), m.p. 118°–121° C, is obtained.

EXAMPLE 7

N-(4',6'-dimethyl-2'-pyridyl)-10α-methoxy-1,6-dimethylergoline-8β-methanamine (I; R = CH₃; n = 1; X = NH; Y = 4,6-(CH₃)₂) — (355/897)

Operating as in Example 1, but employing 4,6-dimethyl-2-aminopyridine, N-(4',6'-dimethyl-2'-pyridyl)-10α-methoxy-1,6-dimethylergoline-8β-methanamine (51% yield), m.p. 187°–190° C, is obtained.

EXAMPLE 8

2'-Pyridyl-10α-methoxy-1,6-dimethylergoline-8β-methyl sulphide (I; R = CH₃; n = 1; X = S; m =o) - (355/907)

To a solution of 5.4 mmol of 2-mercaptopyridine sodium salt in 30 ml of anhydrous dimethylsulphoxide, 4 mmol of 10α-methoxy-1,6-dimethylergoline-8β-methanol tosylate (II; R = CH₃; n = 1) are added.

The solution is kept at 80° C for 2 hours. Most of the solvent is then evaporated in vacuo, and the residue is poured into 200 ml of iced water.

The resulting precipitate is filtered and crystallized from acetone to give 2'-pyridyl-10α-methoxy-1,6-dimethylergoline-8β-methyl sulphide (85% yield), m.p. 193°–194° C.

EXAMPLE 9

5'-Nitro-2'-pyridyl-10α-methoxy-1,6-dimethylergoline-8β-methyl sulphide (I; R = CH₃; n = 1; X = S; Y = 5-NO₂) - (355/926)

Operating as in Example 8, but employing 5-nitro-2-mercaptopyridine, 5'-nitro-2'-pyridyl-10α-methoxy-1,6-dimethylergoline-8β-methyl-sulphide (90% yield), m.p. 102°–105° C is obtained.

What is claimed is:

1. A compound of the formula I:

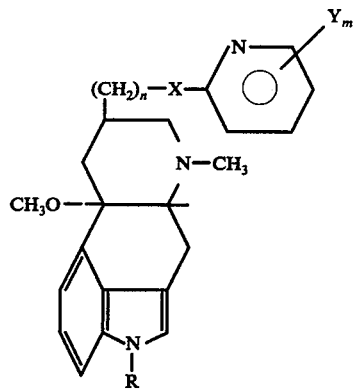

where R is hydrogen or methyl, X is sulphur or the NH group, Y is selected from the class consisting of methyl, methoxy, chlorine, bromine, iodine, nitro or cyano, m is 0, 1 or 2, and n is 1 or 2,
and their pharmaceutically acceptable salts.

2. The compound as defined in claim 1, which is N-(2'-pyridyl)-10α-methoxy-1,6-dimethylergoline-8β-methamine.

3. The compound as defined in claim 1, which is N-(5'-nitro-2'-pyridyl)-10α-methoxy-1,6-dimethylergoline-8β-methanamine.

4. The compound as defined in claim 1, which is N-(3'-nitro-2'-pyridyl)-10α-methoxy-1,6-dimethylergoline-8β-methanamine.

5. The compound as defined in claim 1, which is N-(5'-bromo-2'-pyridyl)-10α-methoxy-1,6-dimethylergoline-8β-methanamine.

6. The compound as defined in claim 1, which is N-(4'-methyl-2'-pyridyl)-10α-methoxy-1,6-dimethylergoline-8β-methanamine.

7. The compound as defined in claim 1, which is N-(5'-methyl-2'-pyridyl)-10α-methoxy-1,6-dimethylergoline-8β-methanamine.

8. The compound as defined in claim 1, which is N-(4',6'-dimethyl-2'-pyridyl)-10α-methoxy-1,6-dimethylergoline-8β-methanamine.

9. The compound as defined in claim 1, which is 2'-Pyridyl-10α-methoxy-1,6-dimethylergoline-8β-methyl sulphide.

10. The compound as defined in claim 1, which is 5'-Nitro-2'-pyridyl-10α-methoxy-1,6-dimethylergoline-8β-methyl sulphide.

* * * * *